US010448636B2

(12) United States Patent
Oliveira

(10) Patent No.: US 10,448,636 B2
(45) Date of Patent: Oct. 22, 2019

(54) ANTI-RESISTANCE METHOD

(71) Applicant: UPL LTD., Mumbai (IN)

(72) Inventor: Gilson Aparecido Hermenegildo de Oliveira, Campinas (BR)

(73) Assignee: UPL LIMITED, Mumbai (IN)

( * ) Notice: Subject to any disclaimer, the term of this patent is extended or adjusted under 35 U.S.C. 154(b) by 0 days.

(21) Appl. No.: 15/535,294

(22) PCT Filed: Dec. 10, 2015

(86) PCT No.: PCT/BR2015/050243
§ 371 (c)(1),
(2) Date: Jun. 12, 2017

(87) PCT Pub. No.: WO2016/090447
PCT Pub. Date: Jun. 16, 2016

(65) Prior Publication Data

US 2017/0360039 A1 Dec. 21, 2017

(30) Foreign Application Priority Data

Dec. 12, 2014 (BR) .......................... 1020140312501

(51) Int. Cl.

| | |
|---|---|
| ***A01N 37/50*** | (2006.01) |
| ***A01N 43/40*** | (2006.01) |
| ***A01N 43/54*** | (2006.01) |
| ***A01N 43/653*** | (2006.01) |
| ***A01N 47/14*** | (2006.01) |
| ***A01N 47/24*** | (2006.01) |
| ***A01N 47/10*** | (2006.01) |

(52) U.S. Cl.
CPC ............. *A01N 37/50* (2013.01); *A01N 43/40* (2013.01); *A01N 43/54* (2013.01); *A01N 43/653* (2013.01); *A01N 47/10* (2013.01); *A01N 47/14* (2013.01); *A01N 47/24* (2013.01)

(58) Field of Classification Search
None
See application file for complete search history.

(56) References Cited

U.S. PATENT DOCUMENTS 9,788,544 B2 * 10/2017 Oliveira ................. A01N 47/14
2002/0173529 A1 * 11/2002 Dutzmann ........... A01N 43/653
514/383

FOREIGN PATENT DOCUMENTS

BR 0617925 * 2/2012

OTHER PUBLICATIONS

Zambolim, L. XLII Brazilian Phytopathology Conference, Rio de Janeiro, Aug. 3-7, 2009 (Year: 2009).*
Revista Cultivar, pp. 8-12. Nov. 2013 (Year: 2013).*

* cited by examiner

*Primary Examiner* — Alton N Pryor
(74) *Attorney, Agent, or Firm* — IP Pundit LLC

(57) ABSTRACT

The decrease in soybean rust control using fungicide mixtures (DMAs+QoIs) reached very low levels for the harvest of 2012/13 (an average of 37% for the three main mixtures). This decrease is due to a decrease in Pp sensitivity to individual DMIs and QoIs, and mixtures thereof. Anti-resistance strategies have not been introduced in Brazil for preventing/delaying the development of resistance of the fungus that is the casual agent of rust (*Phakopsora pachyrhizi*) in soybean [plant form the family Fabaceae, *Glycine max* (L.) Merr.] and of the fungus that is the casual agent of yellow leaf spot (*Drechslera tritici-repentis*) in wheat [plant of the family Triticea, *Triticum aestivum* L.], as well as other disease complexes that attack the main crop plants in Brazil, such as corn, beans, cotton, inter alia. By means of said method it is possible to recover the efficiency of several mixtures (DMI+QoI and QoI+SDHI) due to a decrease in fungal sensitivity. The methods described by the present invention seek to increase the effective useful life of fungicides and increase grain yield.

5 Claims, 3 Drawing Sheets

ANTI-RESISTANCE METHOD

TECHNICAL FIELD OF THE INVENTION

Figure 1:
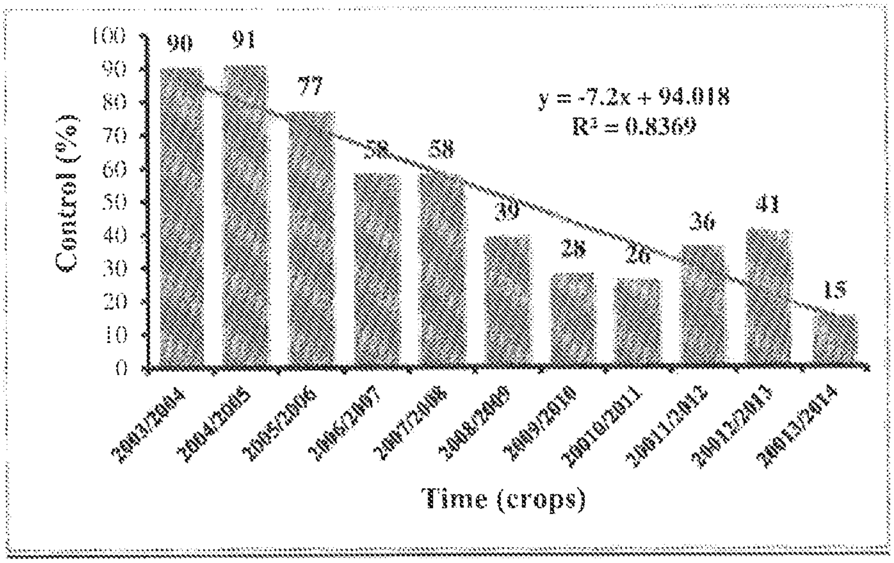

The present invention relates to a method for preventing/delaying the development of resistance of the fungus that is the causal agent of rust (*Phakopsora pachyrhizi*) in soybean [plant from the Family Fabaceae *Glycine max* (L.) Merr.] and of the fungus that is the causal agent of yellow leaf spot (*Drechsiera tritici-repentis*) in wheat [plant of the Family triticeous *Triticum aestivum* L.]. By means of said method it is possible to recover the efficiency of some mixtures (DMI+QoI and QoI+SDHI) due to a decrease in fungal sensitivity. The methods described by the present invention aim at increasing the effective life of fungicides and increase grain yield. Furthermore, said method can also be used for resistance of the causing fungi of other diseases that attack crops plants, such as corn and cotton.

BACKGROUND OF THE INVENTION

In Soybean Cultures.

Two rusts are reported in soybean cultures. The first called American is caused by *Phakopsora meibomiae* Arthur and the second called Asian rust (ASR) caused by *Phakopsora pachyrhizi* Sydow.

The fungus that causes soybean rust belongs to the class of basidiomycetes. The species is called *Phakopsora pachyrhizi* Sydow.

In the specific case of Brazil, the rust was detected in the years 2001/02 and in the very next crop began their control with fungicides. At this time, fungicides "triazoles" alone were applied over a large area with many applications in the soybean production cycle. In the 2005/06 crop some producers (notably in the Brazilian Midwest) complained for the first time, of the rust control failure with the use of these fungicides (mainly DMI). Research conducted in experimental field and laboratory confirmed the reduced sensitivity (resistance) of fungal strains to triazole fungicides.

In the 2013/14 crop were cultivated 29.4 million hectares, with a yield of 3.0 t/ha, with a total production of 82.6 million tons of soybeans.

According to a survey conducted by Kleffmann (2014), in this last soybean crop, on average, three applications/ha were made for the control of *P. pachyrhizi* (Pp). However, in regions where the second crop of soybeans is cultivated up to 11 applications/ha were made in the same area. This practice speeds up the selection of Pp mutants with resistance to fungicides.

The extension of the treated area, the isolated use of fungicides site specific and the large number of applications in the same crop, faced with anti-resistance strategies recommended by the FRAC (2012) to prevent or delay the emergence of resistant strains, show early occurrence of the risk of Pp resistance to fungicides in Brazil.

It is known from the prior art that fungicides used in soybean and wheat crops fall into two chemical groups with site specific mechanism of action, which are: triazoles, or demethylation inhibitors (DMIs)—included therein the tebuconazole, which for a long time was very efficient; and strobilurins, or outside quinone inhibitors (QoIs). More recently a third chemical group has been used, namely the enzyme succinate dehydrogenase inhibitors (SDHI). The combination of the DMIs with QoIs has been used for more than 12 crops for the control of ASR. Additionally, reducing the sensitivity of Pp to DMI burdened fungicidal action of QoIs in the mixtures. From the 2012/13 crop it was noted that Pp sensitivity was reduced to mixtures of DMIs+QoIs and QoIs+SDHI). More than 50% of soybean areas in Brazil receive a second annual crop, which is called "safrinha" (when it is corn/cotton) or "winter crop" (in the southern regions, with winter crops for wheat, oats, canola, rye etc.). This fact causes various populations of fungi to e also be selected, and causes them to become increasingly resistant to fungicides and mixtures above referenced.

In Wheat.

The fungus that causes the yellow leaf spot of wheat belongs to the class of Imperfect Fungi and is called *Drechsiera tritici-repentis* (Died) Shoemaker (Dtr) in anamorphic form and *Pyrenophora tritici-repentis* (Died.) Drechsler in teleomorphic. The yellow leaf spot of wheat was recorded in Australia (Rees & Platz, 1979), Canada (Wright & Sutton, 1990) and the United States (Hosford, 1981). In South America, Dubin (1983) found it in Colombia, Ecuador and Peru. In Argentina it was first observed to the north of Buenos Aires Province in the 1980s (Annone, 1985). In Brazil, the first reference about this disease was made by Costa Neto (1967), having the same being detected in Rio Grande do Sul, in 1959, in the city of Dom Pedrito. Later, Mehta (1975) reported the occurrence of an epidemic of the disease in the state of Parana.

In Brazil, until 1976, it was not allowed the use of fungicides in wheat aerial organs. A milestone for its use was the UNDP/FAO Agreement with the Experimental Station of Passo Fundo, of the Ministry of Agriculture—today Embrapa Wheat.

In wheat crops, on average, three applications per ha/crop are usually made.

According to prior art information, the first attempts to apply fungicides in the aerial part of the wheat crop was around the year 1958 by researchers from the Federal University of Pelotas (today Embrapa Clima Temperado), to control the disease giberela.

At the time, the South-Brazilian Commission of Wheat Research recommended applications of fungicide at booting and flowering, which was used for a decade (between 1976 and 1986), until the recommendation of triadimefom.

In the wheat crop of 2003 technical assistants and producers complained for the first time, about the failure to control leaf spots after continuous use for 20 years of DMI+QoI fungicides.

The area cultivated with wheat crop in 2012/14 reached 2.2 million ha. Control of the disease known as "tan spot of wheat" was made with the use of mixtures, but with very poor (<50%) and inefficient response, due to the development of resistance. Therefore, companies and research institutions are committed to developing an anti-resistance strategy, so that the said disease control efficiency is back to the 80% to 90% level.

Sensitivity Reduction (SR) of Fungi to Fungicides.

It is known that sooner or later, during the years of commercial use of a fungicide, may arise a mutant individual in the target pathogen population that is not sensitive enough to be controlled satisfactorily. It multiplies increasing its population silently.

Generally, the SR is in response to the repeated use of a fungicide with the same mechanism of action, in a large area with many applications in the crop cycle. The first evidence of this change is observed by the producer, that complains about "control failure." In this situation the control went from "efficient and economic" to "inefficient and uneconomical."

With respect to the term "sensitivity reduction", the term "reduction" should be used, preferentially, instead of the term "loss of sensitivity." SR is proven in the lab when there is an increase in sensitivity reduction factor, i.e., SRF (>1).

The term is used to previously sensitive fungal strains, which, through variation mechanism such as mutation, significantly reduced their sensitivity to fungicide (SRF>1.0).

The science of fungicides describes the resistance of a fungus to a fungicide with site specific mechanism of action (for example, DMI, QoI and SDHI) can be cross or multiple. Cross-resistance occurs within the same group, as for triazoles (cyproconazole, epoxiconazole and tebuconazole), and also for strobilurins (azoxystrobin, picoxistrobia, pyraclostrobin and trifloxystrobin). However, it is worth noting the occurrence of multiple resistance when the same strain of the fungus has a reduced sensitivity both with respect to triazoles as with respect to strobilurins.

With regard to soybean, particularly with soybean rust, it is likely that both the cross-resistance and the multiple are occurring; i.e., resistance to all triazoles and all strobilurins. And in wheat, it was proved that only cross-resistance is being checked.

The situation proved, on this account, to be worrying. Faced with this fact, companies and institutions began to wonder what could be done to rescue the control levels (between 80% and 90%) of triazoles and strobilurins, isolated or in mixture.

Reduction of Chemical Control Efficiency a. Soybean Rust—Demethylation Inhibitors (DMIs)-Fungicides As occurred with flutriafol, tebuconazole has become widely used and with high efficiency, being the reference fungicide in controlling rust, but not for long.

In order to clarify the facts, experiments conducted at the Foundation MT, Rondonopolis, by the University of Rio Verde and institutions participating in the Cooperative Tests of Fungicides (beginning in the 2003/04 crop), confirmed the reduction of control efficiency. It was proved the reduction of control effectiveness by comparing the performance of DMIs in the 2005/06 crop with the (2012/13) crop in results of research conducted at the University of Rio Verde. In the 2005/06 crop, the average rust control by DMIs was 90.3. After eight years, corresponding to the 2012/13 crop, the control of DMIs was 52.0 with a reduction in efficacy of 42% (Table 1). (problem)

TABLE 1

Reduced soybean rust control by DMIs fungicides applied preventively in control (%) and control reduction

| | Crops | | Reduction |
|---|---|---|---|
| Fungicide | 2005/06 | 2012/13 | (%) |
| Cyproconazole | 96.0 | 52.0 | 45.9 |
| Epoxiconazole | 80.0 | 40.0 | 50.0 |
| Tebuconazole | 95.0 | 64.0 | 32.8 |
| Average | 90.3 | 52.0 | 42.0 |

Source: Silva et al., 2013.

The reduction of the sensitivity of Pp to tebuconazole and cyproconazole fungicides, controlling only 42 and 38%, respectively, was also demonstrated by Godoy and Palaver (2011). At this time, the mixture still showed no reduction in efficiency; cyproconazole+azoxystrobin, 72% and epoxiconazole+pyraclostrobin, 88% control with an average of the mixtures of 80% of control. Probably, at this time, the efficiency was ensured by QoIs as the average of the DMIs was only 40% (Table 2).

TABLE 2

Control reduction of soybean rust severity, evaluated by the area under the disease progress curve (AUDPC) by some fungicides in crop 2010/11

| Treatments | Severity (%) | Control (%) |
|---|---|---|
| Control | 74.0 a | — |
| Tebuconazole | 49.9 b | 42 |
| Cyproconazole | 58.1 b | 38 |
| Cyproconazole + o azoxystrobin | 14.8 c | 72 |
| Epoxiconazole + pyraclostrobin | 9.0 | 88 |

Source: Modified Data of Godoy and Palaver (2011).

An example that reinforces the reported fact is the gradual reduction of tebuconazole control over the crops using it covering the period beginning in 2004/05 to 2013/14 (as FIG. 1).

From the 2003/04 crop, soybean rust control efficiency (ASR) by tebuconazole, was reduced by 7.2% per year (see also FIG. 1).

Therefore, the fact is that today there is a problem that lies in the fact that with this reduction in speed in two more crops, it is likely that soybean rust control by tebuconazole reaches zero. So again companies are faced with the problem of how producers can take precautions to ensure ASR control over 80%? And yet, what would be the amount of damage from lack of anti-resistance strategy? (problems)

Soybean Rust—QoIs Fungicides

The reduction of control by the mixtures can also be attributed to sensitivity reduction of Pp to QoIs. From the 2008/09 crop was detected early reduction in the control of azoxystrobin and reached only 16% of control in the 2013/14 crop (see FIG. 6).

Figure 6:
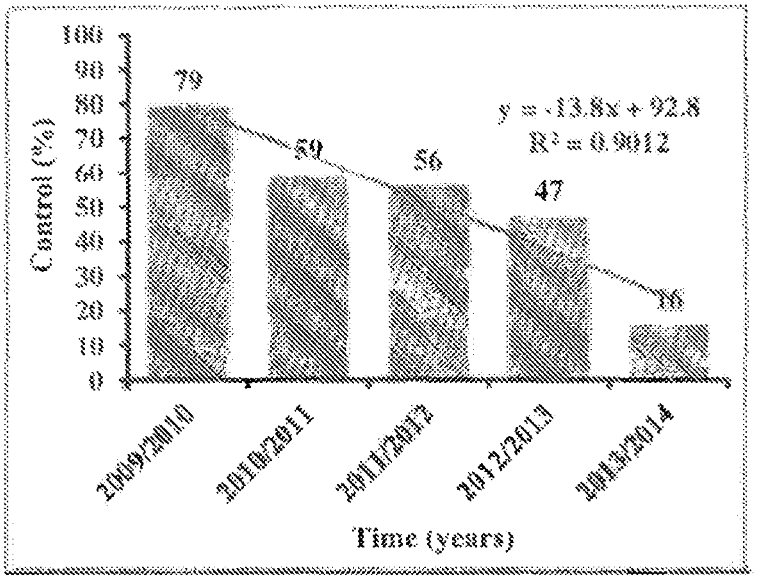

Using the equation y=−13.8x+92.8, it was determined that from 2009/10 the efficacy of this fungicide has been reduced by 13.8% per year and ending by reaching in the 2013/14 crop, only 16% of control (see FIG. 6).

Comparing the reduction of tebuconazole control with the azoxystrobin, the current level of control is similarly low. However, the difference is in the shortest time required by DMI and higher with QoI to achieve this same level "low"

Soybean Rust—Fungicide Mixtures Composed of DMI+QoI

What has been checked with the latest crops is the reduction of rust control by mixtures of triazoles+strobilurins. Questioned whether the low control presented by mixtures can be attributed to greater reduction of the sensitivity of the fungus to DMIs. Or, if the lower control of the mixtures can be attributed to reduced sensitivity of Pp to QoIs.

The results of cooperative tests of fungicides, coordinated by Embrapa Soybean, Londrina, can bring the answer to these questions. The following graphs of FIGS. 2, 3, 4 and 5 show the reduction of rust control by fungicide mixtures traditionally used in soybeans over the past crops.

Figure 2:
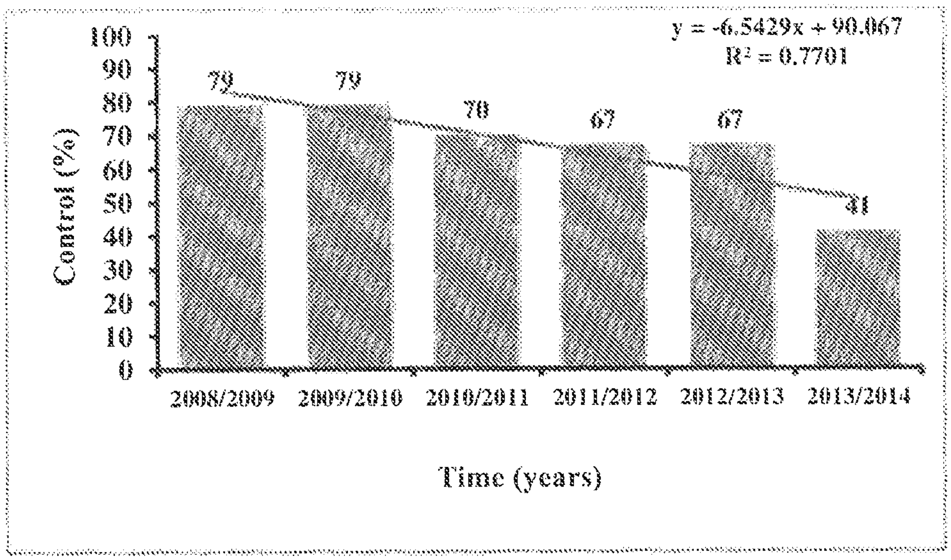

An example with cyproconazole+azoxystrobin mixture is shown in FIG. 2. This mixture has been used since 2003/04, when it exhibited an efficiency of 90%.

Using the equation y=−6.5429x+90.067, you can calculate that from the 2007/08 crop the effectiveness of this mixture has been reduced by 6.54% per year, reaching in the 2013/14 crop only 41% of control (see FIG. 2).

Figure 3:
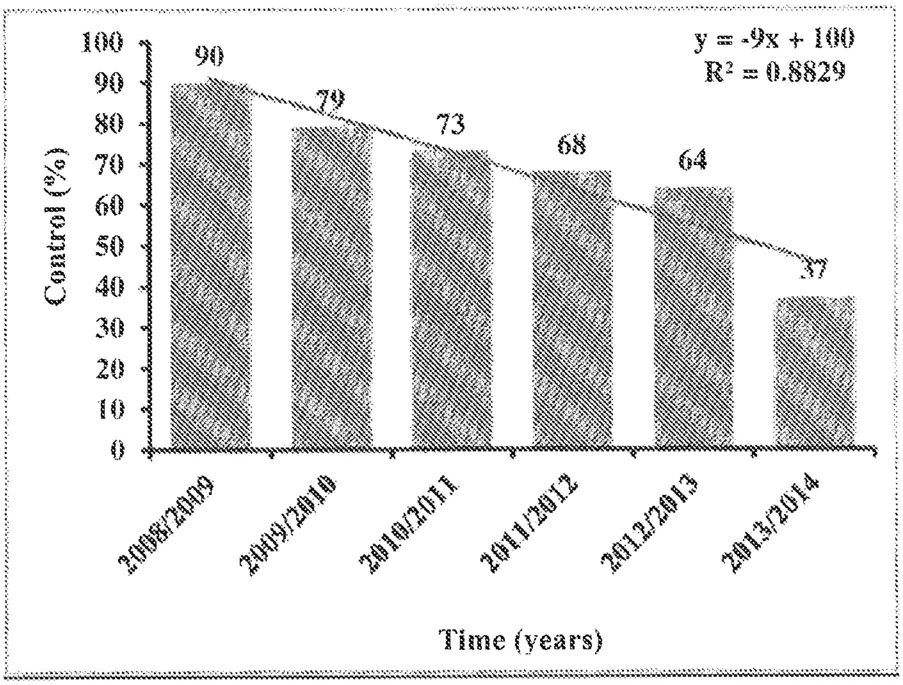

Using the equation y=−9.0x+100.0, one can calculate that from 2008/09 the effectiveness of the mixture cyproconazole+azoxystrobin has been reduced by 9.0% per year, reaching 37% control in the 2013/14 crop (see FIG. 3).

The mixture "epoxiconazole+pyraclostrobin" has been used since 2007/08. With the equation y=−12.6x+99.0 [where y=control (%) and x=the percentage of annual reduction of control], you can calculate that from the 2009/10 crop the effectiveness of this mixture has been decreased by 12.6% per year, reaching in the last crop 23% (see FIG. 4).

Figure 5:
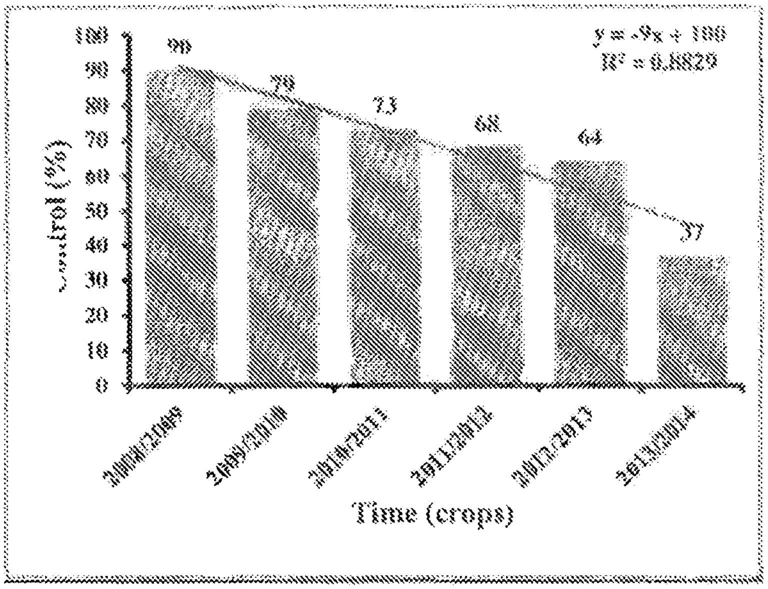

According to the equation y=−9.0x+100.0, from the 2008/09 crop the average effectiveness of mixtures "cyproconazole+azoxystrobin", "cyproconazole+picoxystrobin" and "epoxiconazole+pyraclostrobin" over six crops has been reduced by 9.0% per year, reaching 37% in the last crop (see FIG. 5).

In Wheat

In the 2003 wheat crop for the first time, there was complaint of leaf spot control failure after continuous use of fungicides DMI+QoI, for 20 years. Until that time there were few reports of the sensitivity of the fungus that is causal agent of yellow spot to fungicides (Stolte, 2006; Tonin, 2009; Beard et al, 2009; Patel et al, 2012). The reference concentrations of sensitivity of Dtr to fungicides found in the literature were 0.17 mg/L in average for the epoxiconazole, propiconazole and tebuconazole. Hunger & Brown, determined an IC50 of 0.04 mg/L for propiconazole and 0.19 for tebuconazole; Beard et al, determined IC50 of 0.19 mg/L for epoxiconazole and 0.25 mg/L for tebuconazole). Comparing these values with the sensitivity of isolates of Brazil proves the reduced sensitivity occurring here (see Table 3).

TABLE 3

Concentrations for 50% inhibition of mycelium growth ($IC_{50}$) of five isolated from *Drechsiera siccans* for five fungicides DMIs

| Fungicide | Isolated (IC50 mg/L) | | | | | |
|---|---|---|---|---|---|---|
| | 01/F30 | 02/RZ | 03/SF | 04/F52 | 05/VQ | Average |
| Cyproconazole | 0.36 | 0.47 | 0.32 | 0.44 | 0.29 | 0.37 b |
| Epoxiconazole | 0.28 | 0.28 | 0.40 | 0.32 | 0.40 | 0.33 b |
| Propiconazole | 0.32 | 0.51 | 0.30 | 0.30 | 0.30 | 0.34 b |
| Prothioconazole | 0.22 | <0.1 | 0.26 | 0.25 | 0.14 | 0.21 c |
| Tebuconazole | 0.66 | 0.49 | 0.65 | 0.61 | 0.44 | 0.57 a |
| Average | 0.36 | 0.37 | 0.38 | 0.38 | 0.31 | |
| CV (%) | 9.05 | | | | | |

Averages followed by the same letter do not differ by 5% of the Tukey test. Average of two experiments.

However, the highest reduction of sensitivity of the Dtr to fungicides and what better explains the control failure claimed by producers is the CI50 obtained for QoIs fungicides (see Table 4).

TABLE 4

Inhibitory Concentration of 50% of the spore germination (CI50) of fungicides for five isolates of *Drechsiera tritici-repentis* to strobilurin fungicides

| Fungicide | Isolated ($CI_{50}$ mg/L) | | | | | |
|---|---|---|---|---|---|---|
| | 01/QTZ | 02/ONX | 03/HZT | 04/GUA | 05/CD | Average |
| Azoxystrobin | A > 40 a | A > 40 a | A > 40 a | A > 40 a | A > 40 a | A > 40 a |
| Kresoxim methyl | A > 40 a | A > 40 a | A > 40 a | A > 40 a | A > 40 a | >40 a |
| Picoxystrobin | A > 40 a | A > 40 a | A > 40 a | A > 40 a | A > 40 a | >40 a |
| Pyraclostrobin | D 0.75 b | B 0.85 b | C 0.78 b | E 0.58 b | A 1.03 b | 0.80 b |
| Trifloxystrobin | A > 40 a | A > 40 a | A > 40 a | A > 40 a | A > 40 a | >40 a |
| Average | C > 32.15 | B > 32.17 | C > 32.15 | D > 32.11 | A > 32.20 | |
| CV (%) | 0.02 | | | | | |

Averages followed by the same letter do not differ there between by 5% of the Tukey test. Lowercase compare average in the column and capital letters in the line. Average of two experiments.

Taking as $Cl_{50}$ standard of sensitivity, 0.75 mg/L (Table 4) obtained for pyraclostrobin, it is calculated the reduction factor of the sensitivity of the Dtr to QoIs fungicides (see Table 5).

TABLE 5

Reduction factor of the sensitivity of *Drechslera tritici- repentis* to QoIs fungicides.

| Fungicide | Isolated | | | | | |
|---|---|---|---|---|---|---|
| | 01/QTZ | 02/ONX | 03/HZT | 04/GUA | 05/CD | Average |
| Azoxystrobin | A > 53 a | A > 53 a | A > 53 a | A > 53 a | A > 53 a | >53 a |
| Kresoxim methyl | A > 53 a | A > 53 a | A > 53 a | A > 53 a | A > 53 a | >53 a |
| Picoxystrobin | A > 53 a | A > 53 a | A > 53 a | A > 53 a | A > 53 a | >53 a |
| Pyraclostrobin | D 1.0 b | B 1.13 b | C 1.04 b | E 0.77 b | A 1.37 b | 0.1.1 b |

TABLE 5-continued

Reduction factor of the sensitivity of *Drechslera tritici- repentis* to QoIs fungicides.

| Fungicide | Isolated | | | | | Average |
| --- | --- | --- | --- | --- | --- | --- |
| | 01/QTZ | 02/ONX | 03/HZT | 04/GUA | 05/CD | |
| Trifloxystrobin | A > 53 a | A > 53 a | A > 53 a | A > 53 a | A > 53 a | >53 a |
| CV (%) | 0.02 | | | | | |

CI50 of sensitivity reference of 0.75 mg/L.

When the SRF is close to 1.0 there is no reduction of sensitivity. However, if >1 with different magnitude, it indicates reduced sensitivity of fungi to fungicides. In this case SRF ranged from 1.04 to >53 (see Table 5).

Regarding the state of the art related to patent documents, literature is very broad and comprehensive, although no document reported on the solution to the technical problem, as will be described herein. Just as an example, it stands out:

The aforementioned examples related to soybean and wheat have been so far the most studied due to pathogens Pp and Dt provide amplitude of damage above 50% in their respective crops. However, the concept of resistance should also be extended to all crops including cotton, corn, beans, among others.

Regarding the state of the art related to patent documents, literature is very broad and comprehensive, although no document reported on the solution to the technical problem, as will be described herein. Just as an example, it stands out: International patent application WO 2012040804 A2, entitled: "Synergistic combinations of triazoles, strobilurins and benzimidazoles, uses, formulations, production processes and applications using the same", which describes an agrochemically synergistic formulation of triazoles, strobilurin and benzimidazoles, in specific proportions to control and/or combat pests and diseases in crops. Also described are their preparation process, use and method of use, as well as the use of triazoles, strobilurin and benzimidazoles in the preparation of a synergistic agrochemically formulation of the invention.

European patent application EP 2719280 A1, titled "Use of N-phenylethylpyrazole carboxamide derivatives or salts thereof for resistance management of phytopathogenic fungi," which refers to the use of derivatives of carboxamide pyrazole-ethyl-N-phenyl, in particular 3-difluoromethyl-1-methyl-1H-pyrazole-4-carboxylic acid [2-(2,4-dichlorophenyl)-2-methoxy-1-methylethyl] amide for resistance management of phytopathogenic fungi on crops and describes a method for resistance management of phytopathogenic fungi in various crops.

In view of all the foregoing, in order to recover the control levels of some fungicides, the present invention developed a method for preventing/delaying the development of fungal resistance in some crops such as soybeans, wheat, cotton, corn and beans, more specifically to the fungus that is causal agent of soybean rust and the fungus that is causal agent to yellow leaf spot of wheat.

SUMMARY OF THE INVENTION

The present invention introduces in the Brazilian system of production of soybean, wheat, cotton, corn, beans among others, an anti-resistance highly effective strategy, pioneer of these crops in Brazil. It consists of adding a fungicide "manganese ethylene bis(dithiocarbamate)+Zn" multi site, to any mixtures of fungicides, DMIs, QoIs and SDHI in all combinations and applications.

OBJECTS OF THE INVENTION

Considering the reduction in the control of DMIs, isolates QoIs, and mixtures, the present invention aims to increase the useful life of the fungicidal mixtures "DMIs+QoIs" or "QoIs+SDHIs", now with reduced control due to reduced sensitivity of Pp and Dtr to the mixtures.

Another object of the present invention aims to preserve and/or delay the reduction of the sensitivity of Pp and Dtr mixtures containing "carboxamides+QoI," "prothioconazole+QoI," "prothioconazole+QoI+carboxamide" and "QoI+carboxamides". More precisely, increased fungitoxicity is achieved by adding a multi-site fungicide to the mixtures.

FIG. 1. Reduced soybean rust control by tebuconazole over eleven crops. (Source: Cooperative tests of fungicides).

FIG. 2. Control Reduction of soybean rust by cyproconazole+azoxystrobin mixture over six crops. (Source: Cooperative tests of fungicides).

FIG. 3. Control Reduction of soybean rust by cyproconazole+picoxystrobin mixture over six crops. (Source: Cooperative tests of fungicides).

Figure 4:
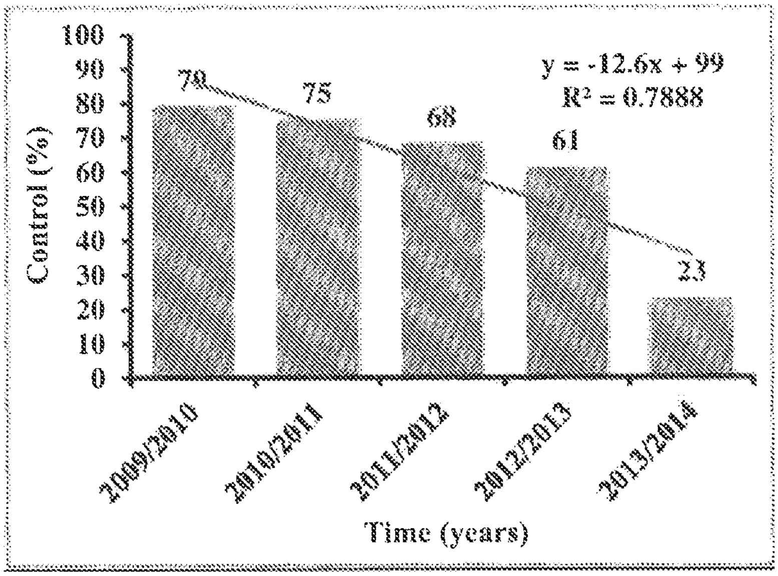

FIG. 4. Reduction control of soybean rust by epoxiconazole+pyraclostrobin mixture over six crops. (Source: Cooperative tests of fungicides).

FIG. 5. Average reduction of soybean rust control by mixtures of cyproconazole+azoxystrobin, cyproconazole+picoxystrobin and epoxiconazole+pyraclostrobin over six crops. (Source: Cooperative tests of fungicides).

FIG. 6. Control Reduction of soybean rust for azoxystrobin over six crops. (Source: Cooperative tests of fungicides).

DETAILED DESCRIPTION OF THE INVENTION

In order to solve some of the problems found in the prior art—that is, to rescue the control levels (between 80% and 90%) of triazoles, strobilurins, carboxamides, isolated or in mixture—the present invention developed a method for preventing/delaying the development of fungal resistance in some crops such as soybeans, wheat, cotton, corn and beans, specifically for the fungus that is the causal agent of rust (*Phakopsora pachyrhizi*) of soybean (plant of the Family Fabaceae *Glycine max* (L.) Merr.), and the fungus that is the causal agent of yellow leaf spot—(*Drechsiera tritici-repentis*) of wheat (plant of the Family triticeous *Triticum aestivum* L.) and all other disease complexes including these two crops and all other disease complexes of grain crops in Brazil such as corn, cotton, beans and other of minor importance.

By the said method it is possible to recover the efficiency of some mixtures (MDI+QoI) due to increased fungitoxicity of mixtures.

The fungus resistance retarding technique consists of:

add to the spray tank, mancozeb (manganese ethylene bis(dithiocarbamate)+Zn), multi-site fungicide, mixtures of demethylation inhibitor fungicides (DMIs), quinone outside inhibitors (QoI) and succinate dehydrogenase inhibitors (SDHI) currently in use. The amount of mancozeb can vary between 1.0 kg/ha and 5.0 kg/ha, preferentially between 1.0 kg/ha and 4.0 kg/ha, most preferentially between 1.0 and 3.0 kg/ha, together with the fungicide (mixture of prefab "DMI+QoI" or "QoI+SDHI") in all of their combinations and applications;

trigger the spray tank agitator; and once the syrup is homogenized, apply the syrup in crops.

The anti-resistance strategy of the present invention is the addition of the multi-site protective fungicide, e.g. mancozeb, mixtures of "DMIs+QoIs" or "QoIs+SDHIs" in control of soybean rust and yellow spot of wheat leaf and other diseases complexes in all crops. The addiction of the multi site protective is given with a first mobile penetrating fungicide (QoI) and subsequently with a second mobile penetrating fungicide (DMI or SDHI).

In the case of soybean rust, the facts showed that the resulting control of the mixtures use of 80% of two fungicides specific site (strobilurins+triazoles) was not durable. So much that, after five crops of continuous use, producers reported the failure of said control.

Experiments conducted at various locations in Brazil showed the efficiency of mancozeb (manganese ethylene bis(dithiocarbamate)) applied alone to control soybean rust and yellow spot of wheat leaf. However, its greatest contribution was proven when added to commercial blends bringing control to values of up to 80%, similar efficiency of mixtures "triazole+strobilurin" at the beginning of its use.

The results showed that the addition of mancozeb improved the performance of all the mixtures tested. Therefore, the present invention used the same strategy as the solution to recover the original control levels (>80%) and make the useful life of the fungicides longer in controlling the target disease of the invention. This is because, mancozeb, being a multi-site protective fungicide and presenting a broad spectrum of action, will also contribute to the control of other diseases in soybean and also in wheat.

It is important to note that the method of the present invention, although quite simple, should be understood as innovative and very important for the sustainability of soybean and wheat cultures in Brazil and worldwide. First, because until then, the control of soybean rust and yellow spot in wheat showed to be inefficient. Second, because with mixtures "triazole+strobilurin" it was the latter that made the control and technical scholars understood that it would not be feasible the development of resistance to strobilurins, which unfortunately ended up happening. This is because the fungus used a new biochemical mechanism, hitherto unknown, to face the fungicide (QoIs) and not be eliminated from the environment.

The method of the present invention aims at increasing the effective life of fungicides and increase grain yield.

It was clearly demonstrated, on the background of the invention, the use of the multi-site protective fungicide "manganese ethylene bis(dithiocarbamate)+Zn" as the mechanism of action for recovering the control efficiency of the mixtures that showed reduced efficacy due to reduced sensitivity of the fungus to these active ingredients.

Thus, in order to solve the prior art drawbacks related primarily to soybean and wheat, the present invention aims to provide a method for treating soybean rust and wheat yellow spot with the addition of multi-site fungicides to the existing commercial mixtures.

The multi-site fungicides, such as mancozeb, act at least in six biochemical mechanisms of the fungus cell, hampered or preventing development of resistance. This is the most reliable tool in the fight against the development of resistance of fungi to fungicides.

EXAMPLES

In Soybean.

A study was conducted to determine the contribution of the mancozeb addition to mixtures of "strobilurin+triazoles." The experiments were conducted in the field, in nine different locations, where it was determined the fungi toxicity of mancozeb to soybean rust.

Two doses were tested (1.5 and 2.0 kg/ha) with various numbers of mancozeb applications. The effect of mancozeb (1.5 kg/ha), incorporated into commercial mixtures was also tested.

The experiments were conducted with soybean cultivar Monsoy 9144 RR. Mancozeb formulation 750 WDG (water dispersible granules) was used, commercially available, for application of mancozeb according to Tables 6 and 7.

TABLE 6

Control (%) of soybean rust by mixing "DMI + QoI" added or not mancozeb, applied three times in two groups of phenological stages of soybean, evaluated by the area under the disease progress curve (AUDPC). Rio Verde - GO

| | Mancozeb | | |
|---|---|---|---|
| Mixtures | Without | With | RI |
| Cyproconazole + Azoxystrobin | 42.8 | 74.0 | 31.2 |
| Cyproconazole + Pycoxistrobin | 74.0 | 79.4 | 5.4 |
| Tebuconazole + Pycoxistrobin | 74.0 | 85.9 | 11.9 |
| Average | A 66.1 | B 79.8 | 13.7 |

Severity in the control = 70%.
CV = 4.60%.
RI = Relative Increase of Control.

TABLE 7

Control (%) of soybean rust by mixtures "DMI + QoI" added or not mancozeb, applied three times at different growth stages and assessed by the severity in leaflet - Passo Fundo - RS

| | Mancozeb | | |
|---|---|---|---|
| Mixtures | Without | With | RI |
| Cyproconazole + Azoxystrobin | 68.6 | 89.8 | 21.2 |
| Epoxiconazole + pyraclostrobin | 40.5 | 75.2 | 34.7 |
| Tebuconazole + Pycoxistrobin | 64.4 | 79.0 | 14.6 |
| Average | A 57.8 | B 81.3 | 23.5 |

Severity in the control = 37.3%.
CV = 6.45%.
RI = Relative Increase of Control.

From the experimental results, we found that the addition of the fungicide protective target not only reduces the risk of resistance, but primarily reverts control to the original level of 80%, and achieve results also in the yield increase of soybean grain.

In wheat. Due to reduced sensitivity of Dtr, mainly to QoIs, control of leaf spot has been very low (15.5% as shown in Table 8).

With the addition of mancozeb, by using the method anti-resistance described in the present invention, the control has been quite improved (33.3% also as shown in Table 8).

TABLE 8

Control (%) of the wheat leaf spots mixtures of DMI + QoI with or without mancozeb added. Evaluation 14 days after the first application

| | Mancozeb | |
|---|---|---|
| Fungicide | Without | With |
| Cyproconazole + Azoxystrobin | 0 | 30 |
| Cipro. + azoxy + propiconazole | 23 | 38 |
| Epoxiconazole + pyraclostrobin | 19 | 36 |
| Tebuconazole + methyl crezoxim | 15 | 39 |
| Tebuconazole + trifloxystrobin | 17 | 29 |
| Prothioconazole + trifloxystrobin | 17 | 28 |
| Average | 15.2 | 33.3 |

Thus, in view of the above reported tests, it was found that the addition of mancozeb increased control of rust and wheat yellow spot with the conventional fungicide "DMI+QoI". This can also be extrapolated to other disease complexes in other crops as above mentioned.

In view of the foregoing it can be said that one advantage of the method described herein is to use the multi site fungicide mancozeb, since hitherto, there are known cases of fungi resistant to it. Therefore, it appears as an essential tool in the fight against soybean rust resistance to fungicides DMIs, QoIs, and mixtures thereof. It was further found that the lower the performance of the mixture in rust control, the greater the added benefit of mancozeb. Furthermore, the addition of the dithiocarbamate (such as mancozeb) resulted in better disease control and plant productivity. Therefore, said method is regarded as innovative and very important for the soybean crop sustainability in Brazil and worldwide.

It was concluded therefore that the addition of a fungicide multi site protective, such as mancozeb, for the combined products (registered for control of Asian soybean rust and wheat yellow spot) regains control and primarily prevents the future development of fungal resistance.

It is important to emphasize that although the present invention has exemplified its application in soybean and wheat cultures, the patent holder states that the method described herein may also be applied to other cultures, such as, for example, corn, cotton and bean.

The present invention is more specifically explained by the examples above. However, it should be understood that the scope of the present invention is not limited to the examples in any respect. It can be seen by one skilled in the art that although the present invention includes the previously reported examples, modifications and changes can be made within the technical scope of the present invention.

The invention claimed is:

1. An anti-resistance method for preventing or delaying the development of a fungal disease in a soybean or wheat crop, the method comprising:

(i) adding to a spray tank, mancozeb (manganese ethylene bis(dithiocarbamate)+Zn) in an amount of 1.0 kg/ha to 5.0 kg/ha, and a prefabricated mixture of fungicides comprising:

a quinone outside inhibitor fungicide (QoI), which is a strobilurin, and a demethylation inhibitor fungicide (DMI), which is a triazole;

(ii) triggering spray tank agitator to form a homogenized syrup; and (iii) applying the homogenized syrup to the crop;

wherein *Phakopsora pachyrhizi* is a causal agent of rust in the soybean crop, and *Drechslera tritici-repentis* is a causal agent of yellow leaf spot in the wheat crop, and wherein the addition of the mancozeb to the quinone outside inhibitor and the demethylation inhibitor increases the resistance of the crop to the disease in comparison to the method lacking mancozeb.

2. The method according to claim 1, wherein applying the homogenized syrup rescues control levels of the disease between 80% and 90%.

3. The method according to claim 1, wherein the application of the homogenized syrup preserves or retards sensitivity reduction of *P. pachyrhizi* and *Drechsiera tritici-repentis* of the mixture comprising prothioconazole as the demethylation inhibitor.

4. The method according to claim 1, wherein the mancozeb is added in the amount between 1.0 and 4.0 kg/ha.

5. The method according to claim 1, wherein the mancozeb is added in the amount between 1.0 kg/ha and 3.0 kg/ha.

* * * * *